US00PP11794P2

(12) United States Plant Patent
Brown

(10) Patent No.: US PP11,794 P2
(45) Date of Patent: Mar. 6, 2001

(54) AGLAONEMA PLANT NAMED 'JUBILEE PETITE'

(75) Inventor: B. Frank Brown, Malabar, FL (US)

(73) Assignee: Sunshine Foliage World, Zolfo Springs, FL (US)

( * ) Notice: Subject to any disclaimer, the term of this patent is extended or adjusted under 35 U.S.C. 154(b) by 0 days.

(21) Appl. No.: 09/291,099

(22) Filed: Apr. 14, 1999

(51) Int. Cl.[7] ..... A01H 5/00

(52) U.S. Cl. ..... Plt./376

(58) Field of Search ..... Plt./376

(56) References Cited

U.S. PATENT DOCUMENTS

P.P. 10,280 * 3/1998 Brown ..... Plt./376

* cited by examiner

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Aglaonema named 'Jubilee Petite' particularly characterized by its upright, outwardly arching, compact and uniform plant habit; freely clumping growth habit; short internodes giving a very full and dense appearance; upper leaf surfaces that are dark green at the margins with distinct silver green centers and random spots; relatively small and lanceolate-shaped leaves; green petioles; and tolerance to low temperatures.

2 Drawing Sheets

BACKGROUND OF THE INVENTION

The present invention relates to a new and distinct cultivar of Aglaonema plant, botanically known as Aglaonema hybrid, and hereinafter referred to by the cultivar name 'Jubilee Petite'.

The new Aglaonema is a product of a planned breeding program conducted by the Inventor in Valkaria, Fla. The objective of the breeding program was to develop new compact Aglaonemas with unique and interesting leaf patterns that readily produced divisions.

The new Aglaonema originated from a cross made by the Inventor in December, 1982, of an unnamed selection of *Aglaonema nitidum f. curtisii* as the female, or seed, parent with an Aglaonema hybrid var. Tricolor, not patented, as the male, or pollen, parent. The cultivar 'Jubilee Petite' was discovered and selected by the Inventor in 1983 as a seedling within the progeny of the stated cross in a controlled environment in Valkaria, Fla.

Plants of the new Aglaonema differ from plants of the femal parent primarily in leaf pattern. In addition, plants of the new Aglaonema are much more freely clumping than plants of the female parent.

Plants of the new Aglaonema differ from plants of the male parent in leaf pattern and petiole coloration. In addition, plants of the new Aglaonema are more compact, smaller and can tolerate much lower temperatures than plants of the male parent.

Asexual propagation of the new cultivar by cuttings and by divisions at Valkaria, Fla. has shown that the unique features of this new Aglaonema plant are stable and reproduced true to type in successive generations.

SUMMARY OF THE INVENTION

The new Aglaonema has not been observed under all possible environmental conditions. The phenotype may vary somewhat with variations in environment such as temperature, light intensity, fertilizer rate, and/or irrigation amount and frequency without, however, any variance in genotype.

The following traits have been repeatedly observed and are determined to be the unique characteristics of 'Jubilee Petite'. These characteristics in combination distinguish 'Jubilee Petite' as a new and distinct cultivar:

1. Plants of the Aglaonema are upright and outwardly arching in plant habit.

2. Plants of the new Aglaonema maintain a compact and uniform plant habit and grow to about 45 cm in height and about 55 cm in width.

3. Plants of the new Aglaonema are freely clumping and readily produce divisions. Removal of center stem enhances production of divisions.

4. Plants of the new Aglaonema have short internodes giving plants a very full and dense appearance.

5. The upper surfaces of mature leaves of plants of the new Aglaonema are dark green at the margins with distinct silver green centers and random spots.

6. Leaves of the new Aglaonema are relatively small and lanceolate with green petioles.

7. Plants of the new Aglaonema are very tolerant of low temperatures, that is, ambient temperatures of about 3° C. do not typically cause foliar damage.

The new Aglaonema can be compared to the commercial *Aglaonema* hybrid cultivar 'Jubilee', disclosed in U.S. Plant Pat. No. 10,270. In side-by-side comparisons conducted by the Inventor in Valkaria, Fla., plants of the new Aglaonema are much smaller, more compact and bushier than plants of the cultivar 'Jubilee'.

The new Aglaonema can be compared to the commercial *Aglaonema* hybrid cultivar 'Maria', not patented. In side-by-side comparisons conducted by the Inventor in Valkaria, Fla., plants of the new Aglaonema are faster growing and leaf coloration is brighter than plants of the cultivar 'Maria'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a side perspective view of a typical plant of 'Jubilee Petite' about 12 to 14 months old and grown in a 25.5-cm container.

The photograph at the top of the second sheet comprises a close-up view of typical young and mature leaves of 'Jubilee Petite'.

The photograph at the bottom of the second sheet comprises a close-up view of the upper and lower surfaces of mature leaves of 'Jubilee Petite'. Leaf colors in the photographs may appear different from the actual colors due to light reflectance.

DETAILED BOTANICAL DESCRIPTION

The following observations, measurements and comparisons describe plants that were about 12 to 14 months old and grown in 25.5-cm containers in Zolfo Springs, Fla., under a polypropylene-covered shadehouse and conditions which closely approximate those used in horticultural practice. Plants were grown under day and night temperatures averaging 27 and 21° C., respectively. The polypropylene shade provided a 80 percent decrease in ambient light level. In the following description, color references are made to The Royal Horticultural Society Colour Chart except where general terms of ordinary dictionary significance are used.

Botanical classification: Aglaonema hybrid cultivar 'Petite'.

Parentage:

*Female, or seed, parent.*—Unnamed selection of *Aglaonema nitidum f. curtisii.*

*Male, or pollen, parent.*—Aglaonema hybrid var. Tricolor, not patented.

Propagation:

*Type.*—By cuttings.

*Time to initiate roots.*—About 28 days at 24° C.

*Time to develop roots.*—About 40 days at 24° C.

*Root description.*—Thick white roots with fine laterals.

Plant description:

*Plant shape.*—Upright and outwardly arching.

*Growth habit.*—Erect when young, becoming outwardly arching with development. Appropriate for 12.5 to 25.5-cm containers. Plants readily produce divisions.

*Plant size.*—Height, soil surface to top of leaf canopy: About 45 cm. Width: About 55 cm.

*Plant vigor.*—Moderate, rapid growth rate.

*Stem description.*—Diameter at soil surface: About 2 cm. Internode length: About 1.5 cm. Color, mature: At soil level, whitish yellow; above soil level, light green, close to 144A.

*Foliage description.*—Shape: Lanceolate. Length, fully expanded: About 17 cm. Width, fully expanded: About 6.75 cm. Margin: Entire. Apex: Acuminate. Base: Cuneate to obtuse. Aspect: Flat to folded upright longitudinally. Texture: Leathery, smooth, glabrous, slightly glossy on both surfaces. Color: Young, upper surface: Margins and random spots/streaks: Close to 146A to 147A. Center and random spots/streaks: Close to 146B and 146C to 146D. Young, lower surface: Close to 146B to 146C. Mature, upper surface: Margins and random spots/streaks: Much darker than 147A. Center and random spots/streaks: Close to 194A to 194B and also some close to 191A to 191B. Mature, lower surface: Greener than 147B to close to 147A. Petiole length, primary shoot: About 20 cm. Petiole diameter at apex: About 5 mm. Petiole diameter at base: About 1.25 cm. Petiole wing: Apparent on lower 60 percent of mature leaf petiole, about 12 cm in length and about 5 mm in width. Petiole (including wing) color: Green, close to 146A.

*Inflorescence.*—Typical of Aglaonema.

Disease tolerance: Plants of the new Aglaonema have exhibited resistance to diseases common to Aglaonema.

Low temperature tolerance: Plants of the new Aglaonema are very tolerant of low temperatures, that is, ambient temperatures of about 3° C. do not cause foliar damage.

It is claimed:

1. A new and distinct cultivar of Aglaonema plant named 'Jubilee Petite', as illustrated and described.

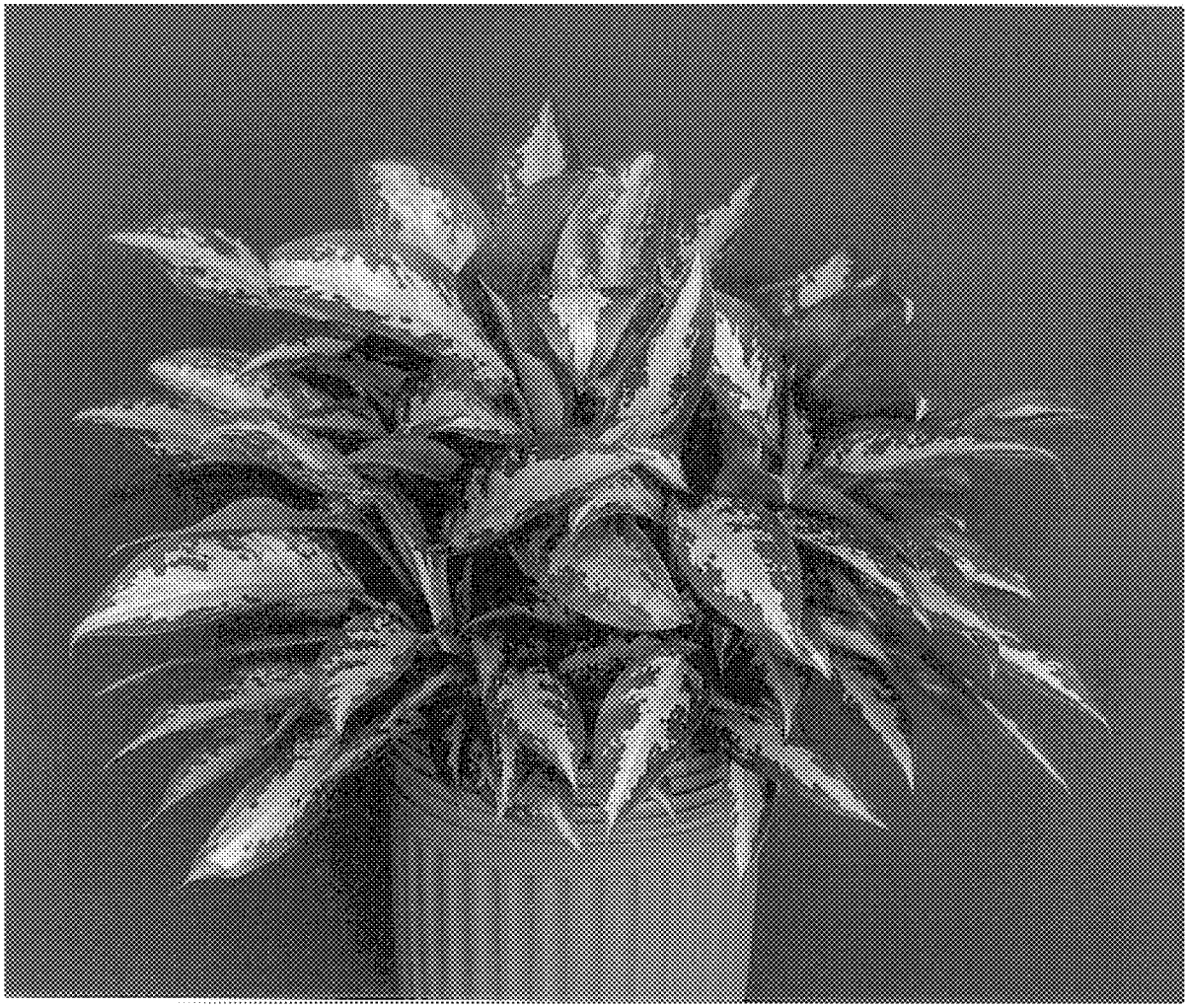

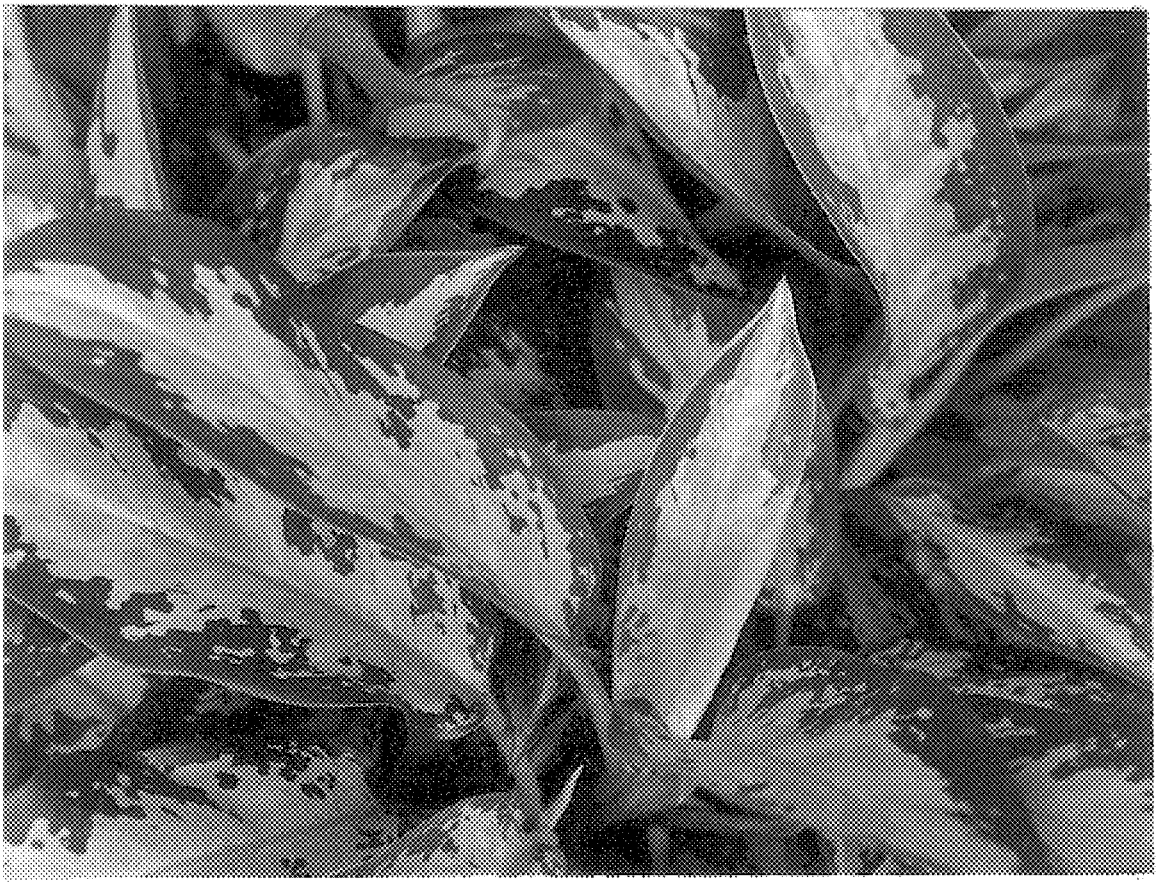
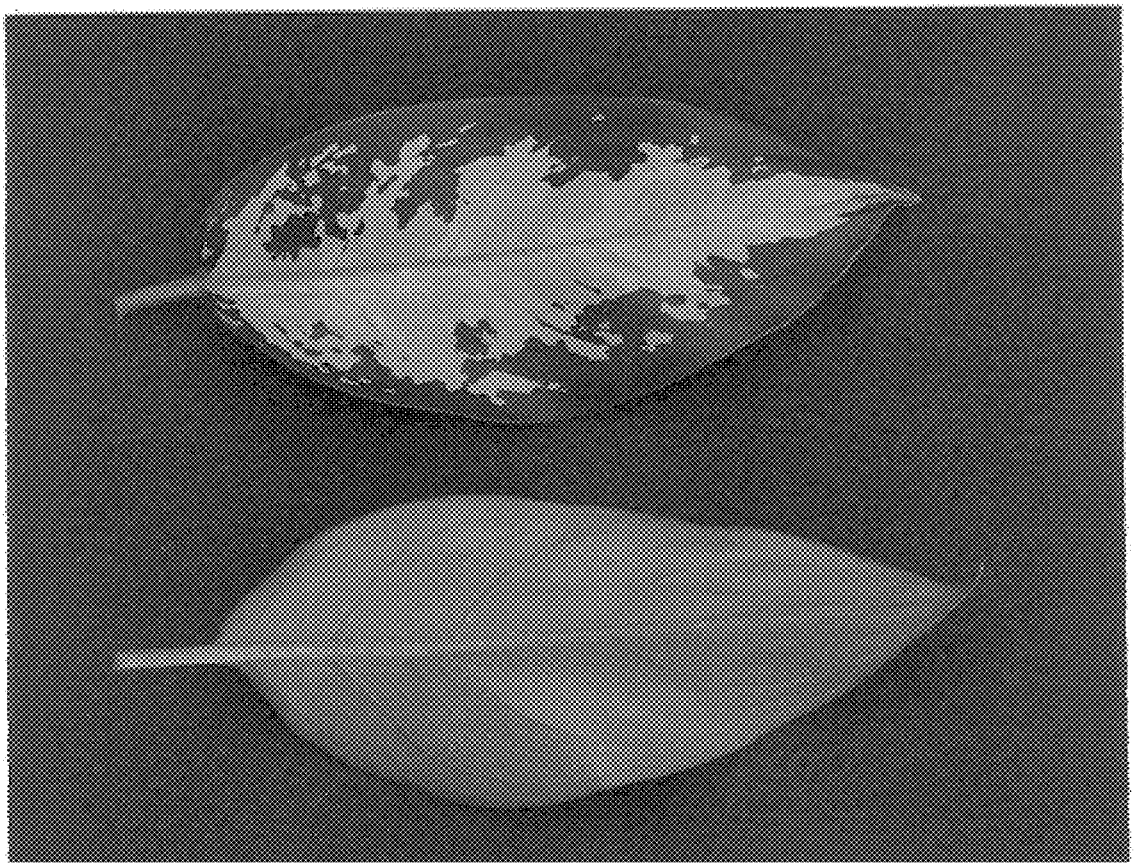

* * * * *